US009339215B2

(12) United States Patent
Van Vugt et al.

(10) Patent No.: US 9,339,215 B2
(45) Date of Patent: May 17, 2016

(54) METHOD AND APPARATUS FOR MONITORING MOVEMENT AND BREATHING OF MULTIPLE SUBJECTS IN A COMMON BED

(75) Inventors: Henriette Christine Van Vugt, Utrecht (NL); Adrienne Heinrich, Den Bosch (NL)

(73) Assignee: Koninklijke Philips N.V., Eindhoven (NL)

( * ) Notice: Subject to any disclaimer, the term of this patent is extended or adjusted under 35 U.S.C. 154(b) by 221 days.

(21) Appl. No.: 14/116,781

(22) PCT Filed: May 24, 2012

(86) PCT No.: PCT/IB2012/052605
§ 371 (c)(1),
(2), (4) Date: Nov. 11, 2013

(87) PCT Pub. No.: WO2012/164453
PCT Pub. Date: Dec. 6, 2012

(65) Prior Publication Data
US 2015/0073283 A1 Mar. 12, 2015

(30) Foreign Application Priority Data
May 30, 2011 (EP) ..................................... 11305655

(51) Int. Cl.
*A61B 5/113* (2006.01)
*G06T 7/20* (2006.01)
(Continued)

(52) U.S. Cl.
CPC ............... *A61B 5/113* (2013.01); *A61B 5/0816* (2013.01); *A61B 5/4806* (2013.01);
(Continued)

(58) Field of Classification Search
CPC .... A61B 5/113; A61B 5/0816; A61B 5/4806; A61B 5/7278; G06T 7/2006; G06T 2207/10016; G06T 2207/20021; G06T 2207/30196
See application file for complete search history.

(56) References Cited

U.S. PATENT DOCUMENTS

| 7,431,700 B2 | 10/2008 | Aoki et al. |
| 2004/0145658 A1 | 7/2004 | Lev-Ran et al. |
| 2013/0035599 A1* | 2/2013 | De Bruijn et al. ... A61B 5/1135 600/476 |

FOREIGN PATENT DOCUMENTS

| EP | 1410755 A1 | 4/2004 |
| WO | 9427408 A1 | 11/1994 |
| WO | 2010070463 A1 | 6/2010 |

OTHER PUBLICATIONS

Kazuki Nakajima et al, "A Method for Measuring Respiration and Physical Activity in Bed by Optical Flow Analysis", Proceedings—19th International Conference—IEEE/EMBS, Oct. 30-Nov. 2, 1997, Chicago, IL, USA.
(Continued)

*Primary Examiner* — Bo J Peng

(57) ABSTRACT

The invention relates to methods and apparatus for monitoring movement and breathing of two or more subjects occupying common bedding. Particularly, the invention relates to a method for monitoring movement of subjects located in a common bedding, the method comprising the steps of: —imaging the bedding by an optical sensor; —performing a motion estimation by producing motion vectors indicating the local displacement of corresponding image blocks between consecutive images, or images that are several frames apart, received from said optical sensor; —calculating motion clusters by measuring spatial and temporal correlations of the motion vectors; —segmenting the calculated motion clusters by assignment of each motion cluster to a corresponding subject, wherein the assignment of the motion clusters to the corresponding subject is based on the spatial and/or temporal similarity of the motion clusters among each other and on previous segmentation results.

19 Claims, 6 Drawing Sheets

(51) Int. Cl.
*A61B 5/08* (2006.01)
*A61B 5/00* (2006.01)

(52) U.S. Cl.
CPC ............ *A61B 5/7278* (2013.01); *G06T 7/2006* (2013.01); *G06T 2207/10016* (2013.01); *G06T 2207/20021* (2013.01); *G06T 2207/30196* (2013.01)

(56) References Cited

OTHER PUBLICATIONS

Kasuki Nakajima et al, A Monitor for Posture Changes and Repiration in Bed Using Real Time Image Sequence Analysis, Proceedings of the 22nd Annual International Conference, Jul. 23-28, 2000, Chicago, IL, USA, pp. 51 to 54.

Yung-Ming Kuo et al, "A Visual Context-Awareness-Based Sleeping-Respiration Measurement System", IEEE Transactions on Information Technology in Biomedicine, vol. 14, No. 2, pp. 255-265, Mar. 2010.

Kazuki Nakajima et al, "Development of real-time image sequence analysis for evaluating posture change and respiratory rate of a subject in bed", Physiological Measurement, Institute of Physics Publishing Bristol, GB, vol. 22, No. 3, Aug. 1, 2001, pp. N21-N28.

Hianbo Shi et al, Motion Segmentation and Tracking Using Normalized Cuts, Sixth International Conference on Computer Vision, Jan. 7, 1998, Narosa, New Delhi, pp. 1154-1160.

Kannappan Palaniappan et al, "Moving Object Segmentation Using the Flux Tensor for Biological Video Microscopy", Advances in Multimedia Information Processing A PCM, Dec. 11, 2007, Lecture Notes in Computer Science, Springer Berlin Heidelberg, Berlin, Heidelberg, pp. 483-493.

Gerard De Haan et al, "True-Motion Estimation with 3-D Recursive Search Block Matching", IEEE Transactions on Circuits and Systems for Video Technology, vol. 3, No. 5, Oct. 1993, pp. 367-379.

\* cited by examiner

METHOD AND APPARATUS FOR MONITORING MOVEMENT AND BREATHING OF MULTIPLE SUBJECTS IN A COMMON BED

CROSS-REFERENCE TO PRIOR APPLICATIONS

This application is the U.S. National Phase application under 35 U.S.C. §371 of International Application No. PCT/IB2012/052605, filed on May 24, 2012, which claims the benefit of European Patent Application No. 11305655.0, filed on May 30, 2011. These applications are hereby incorporated by reference herein.

FIELD OF THE INVENTION

The invention relates to a method and an apparatus for monitoring movement and breathing in common bedding, e.g. bed partners. Particularly, the invention relates to a method for monitoring movement of subjects located in a common bedding, the method comprising the steps of:
  imaging the bedding by an optical sensor;
  performing a motion estimation by producing motion vectors indicating the local displacement of corresponding image blocks between consecutive images, or images that are several frames apart, received from said optical sensor;
  calculating motion clusters by measuring spatial and temporal correlations of the motion vectors;
  segmenting the calculated motion clusters by assignment of each motion cluster to a corresponding subject,
wherein assignment of the motion clusters to the corresponding subject is based on the spatial and/or temporal similarity of the motion clusters among each other and the previous motion assignment results.

BACKGROUND OF THE INVENTION

Breathing is a highly relevant sleep parameter, for example, it provides insight into the state of, among other things, relaxation, sleep depth, apnea and snoring events. Movement is also a highly relevant sleep parameter, for example, it provides insight into the sleep-wake state of the person, and periodic limb movements. More than one person in a bed poses difficulties for monitoring breathing and movement in the bed. This is not only true when two people sleep close together but also when sleeping less close together but under the same duvet. Therefore, this invention relates to monitoring breathing and movement, when two or more subjects share a common bed. In this concern, "subject" should be understood as person and/or animal, while a common bed should be understood as a resting place, like e.g. a bed, which is commonly used by at least two subjects at the same time.

Breathing can be monitored in a contactless way using optical sensors and small microphones. Monitoring breathing can be useful for many sleep/relaxation applications, such as a closed-loop paced breathing device or other relaxation devices, a device for monitoring the various types of apnea or snoring, a sleep coach, a sleep depth monitor, a contactless "sleep quality scorer", etc. Movement during sleep is also a highly relevant sleep parameter, for example, it provides insight into the sleep-wake state of the person, and periodic limb movements. Movement can be monitored in a contactless way using optical sensors, too. Monitoring movement can be useful for several sleep/relaxation applications, such as systems that respond to the sleep/wake state of a person (e.g. a system that turns off when a person falls asleep), a device for monitoring periodic limb movements, a sleep depth monitor, a contactless "sleep quality scorer," etc.

The above devices are typically targeted at monitoring or influencing one user; however, many people share their bed with a bed partner. Bed partners may sleep more or less close together. Multiple couple sleeping positions exist, for example:
  "Sailing away"—the partners are sleeping in the furthest corner of the bed, or head to foot;
  "The Hug"—the partners sleep with their partner face to face in a deep hug;
  "The Spoon"—one partner is lying on their side and the other partner is lying behind this partner with one arm around him or her;
  "Loosely tight"—this position is similar to "The Spoon", but the difference is that one partner keeps some distance between them and their partner; nevertheless, there is always a contact between both partners: a knee, a hand, a foot, etc.

Many people sleep together in one bed, and under one duvet. A survey by the National Sleep Foundation polling over a thousand adult respondents found that on most nights, 61% of the respondents sleep with a significant other, 12% sleep most nights with their pet, and 5% sleep with their child(ren). More than six in ten respondents (62%) report that they prefer to sleep with their significant other.

On-body sensors can be used to monitor movements (e.g. actigraphs) or breathing during sleep (e.g. respiratory belts worn around the chest or/and abdomen), however, these sensors are neither comfortable nor convenient for the user. Off-body sensors, such as optical sensors, are therefore more ideal for the user and have the potential to monitor sleep in an even more reliable way.

Sleeping together poses difficulties for monitoring breathing and/or movement by an off-body sensor which has a fixed location during the night. This is not only true when two people sleep physically close together but also when sleeping less close together yet under the same duvet, because both large and smaller movements, including breathing movements, may travel from one side of the bed to the other.

The paper, "A method for measuring respiration and physical activity in bed by optical flow analysis," by Nakajima et al., in *Proceedings—19$^{th}$ Int. Conference IEEE/EMBS*, Oct. 30-Nov. 2, 1997 Chicago, Ill., USA, discloses a fully noncontact and unconstrained monitoring method, based on optical flow detection of body movement by introducing image sequence analysis. A spatiotemporal local optimization method is applied to determine optical flow in the image sequence. The optical flow visualizes the apparent velocity field of the entire body motion, including breast movement due to respiration and posture changes in bed. A temporal increase in heart rate reflects the magnitude of physical activities. Two candidate parameters are proposed for evaluation of respiratory and physical activities based on a comparison of the experimental results. The average of squared motion velocities reflects the magnitude of physical activities. The representative field-averaged component shows a waveform with periodic fluctuation corresponding to that of respiration obtained with a nasal thermistor.

The paper, "A monitor for posture changes and respiration in bed using real time image sequence analysis," by Nakajima et al., in *Proceedings of the 22$^{nd}$ annual EMBS international conference*, Jul. 23-28, 2000, Chicago, Ill., USA, disclosed a real time system of image sequence analysis to evaluate both a subject's posture changes and respiration in bed. The system consists of a CCD video camera (used as the sensor), an image processing board and a PC. An image processing board that includes 256 CPUs detects the optical flow (apparent velocity) of 256×240 pixels within 150 ms. The representative field-averaged velocity shows a waveform including two components with large peaks and a periodic fluctuation. The large peaks occur during posture change, and the periodic fluctuation corresponds to respiration obtained with a nasal thermistor. The system was tested in a nursing home, where it worked for fifty-six hours in total without problems.

The paper, "A visual context-awareness-based sleeping-respiration measurement system", by Kuo et al., in *IEEE Transactions on Information Technology in Biomedicine*, Vol. 14, No. 2, March 2010, disclosed that due to the rapid growth of the elderly population, improving specific aspects of elderly healthcare has become more important. Sleep monitoring systems for the elderly are rare. In this paper, a visual context-aware-based sleeping-respiration measurement system is proposed that measures the respiration information of elderly sleepers. Accurate respiration measurement requires considering all possible contexts for the sleeping person. The proposed system consists of a body-motion-context-detection context-detection subsystem, a respiration-context-detection subsystem, and a fast motion-vector-estimation-based respiration measurement subsystem. The system yielded accurate respiratory measurements for the study population.

U.S. Pat. No. 7,431,700 B2 discloses a monitor which can detect the respiration of a sleeping person without being affected by the indoor illumination light and can easily evaluate detected respiration quantitatively through image measurement. The monitor comprises a means for projecting a specified illumination pattern, a means for picking up the image of projected light continuously, a means for calculating inter-frame movement of the illumination pattern from the images of two frames acquired by the image pickup means at different times, a means for generating a movement waveform data comprising inter-frame movements arranged in a time series, and a mean for detecting the movement of an object from the movement waveform data.

SUMMARY OF THE INVENTION

It is therefore an object of this invention to improve the preciseness of monitoring breathing and movement by an off-body sensor, especially when two or more subjects share a bed.

This object of the invention is achieved by a method for monitoring movement of subjects located in a common bedding, the method comprising the steps of:
  imaging the bedding by an optical sensor;
  performing a motion estimation by producing motion vectors indicating the local displacement of corresponding image blocks between consecutive images, or images that are several frames apart, (the number of frames depends on the frame rate set in the camera), received from said optical sensor;
  calculating motion clusters by measuring spatial and temporal correlations of the motion vectors;
  segmenting the calculated motion clusters by assignment of each motion cluster to a corresponding subject,
  wherein assignment of the motion clusters to the corresponding subject is based on the spatial and/or temporal similarity of the motion clusters among each other and previous motion vector assignments.

With the invention a technology is proposed with an optical sensor which can adaptively assign image parts to one subject or/and the other in order to analyze a subject's own movements and breathing rhythm correctly throughout the night. This holds even when the subjects sleep on two separate mattresses as well as when they are lying closely together and under the same duvet. Moreover, the proposed technology utilizes only one sensor to simultaneously monitor multiple subjects in bed.

Imaging in this concern should be understood as gathering optical information on the subjects in a common bed. However, there is no need for this optical information to be taken by high resolution camera systems. For performing the motion estimation low resolution images, for example, assembled from an optical sensor similar to the optical sensor used in an optical mouse with a resolution of 16×16 pixels. The low resolution image processing reduces the need for processing power, which in turn makes the method faster even when only small processing systems are used. Additionally, the use of low resolution images enables the anonymous monitoring of subjects with unrecognizable features such as the face. Further, the optical information does not need to be in the visible range of the electromagnetic spectrum. For example, optical information may be assembled in the infrared (IR) range of the electromagnetic spectrum. The use of IR offers the benefit that the method is even less disturbing to the monitored subjects since it is not visible to the naked eye, and therefore more comfortable.

For the motion estimation any kind of algorithm providing suitable motion vectors is applicable, e.g., the algorithm proposed in the paper, "True-motion estimation with 3-D recursive search block matching," by de Haan et al., in *IEEE Transactions on Circuits and Systems for Video Technology*, Vol. 3, No. 5, October 1993. However, in general, any algorithm that computes motion information can be applied, for example, optical flow estimation, maximum a posteriori probability estimation, Markov random field estimation, mean square error calculation, sum of absolute difference calculation, mean absolute differences calculation, sum of squared error calculation, and sum of absolute transformed differences calculation, are applicable for the inventive method.

According to an embodiment of the invention, the segmentation results of prior images are taken into consideration for the assignment of motion clusters to a corresponding subject in a subsequent image. By doing so, the preciseness of the assignment is increased while the processing power required decreases.

According to another embodiment of the invention, a respiration analysis is performed for each subject in the common bed based on the data from consecutive images, or images that are several frames apart, (the number of frames depends on the frame rate set in the camera), provided by the optical sensor.

Measuring respiration is valuable in healthcare and consumer markets. In healthcare, a large number of diseases (e.g. heart failure, respiratory or lung diseases, kidney failure) can be recognized by analyzing a subject's respiratory pattern. For example, when heart failure is advanced, Cheyne-Stokes respiration (periodic breathing) may develop. The following describes how symptoms of heart failure may manifest themselves in particular breathing patterns. Symptoms of heart failure may begin suddenly, especially if the cause is a heart attack. However, most people have no symptoms when the heart first begins to develop problems. Symptoms then develop gradually over days, months or years. The most common symptoms are shortness of breath and fatigue. Heart failure may stabilize for periods of time but often progresses slowly and insidiously. Right-sided heart failure and left-sided heart failure produce different symptoms. Although both types of heart failure may be present, the symptoms of failure of one side are often predominating. Eventually, left-sided heart failure causes right-sided failure. Left-sided heart failure leads to fluid accumulation in the lungs, which causes shortness of breath. At first, shortness of breath occurs only during exertion, but as heart failure progresses, it occurs with less and less exertion and eventually occurs even at rest. People with severe left-sided heart failure may be short of breath when lying down, (a condition called orthopnea), because gravity causes more fluid to move into the lungs. Sitting up causes some of the fluid to drain to the bottom of the lungs and makes breathing easier. When heart failure is advanced, Cheyne-Stokes respiration (periodic breathing) may develop. In this unusual pattern of breathing, a person breathes rapidly and deeply, then more slowly, then not at all for several seconds. Cheyne-Stokes respiration develops because blood flow to the brain is reduced and the areas of the brain that control breathing therefore do not receive enough oxygen. Some people with heart failure experience orthopnea, paroxysmal nocturnal dyspnea, or both. Orthopnea is shortness of breath when a person lies down that is relieved by sitting up. Paroxysmal nocturnal dyspnea is a sudden, often terrifying, attack of shortness of breath during sleep. This condition is an extreme form of orthopnea and a sign of severe heart failure. Dyspnea can also occur in people who have anemia or blood loss because of a decreased number of red blood cells, which carry oxygen to the tissues. The person breathes rapidly and deeply, in a reflexive effort to try to increase the amount of oxygen in the blood. Someone with severe kidney failure, sudden worsening of diabetes mellitus or someone who has taken certain drugs or poisons feels out of breath and may begin to pant quickly because of an accumulation of a large amount of acids in the blood (a condition called metabolic acidosis). Anemia and heart failure may also contribute to dyspnea in people with kidney failure. Additionally, There are three forms of sleep apnea: central (CSA), obstructive (OSA), and complex or mixed sleep apnea (i.e., a combination of central and obstructive). In CSA, breathing is interrupted by a lack of respiratory effort; in OSA, breathing is interrupted by a physical block to airflow despite respiratory effort, and snoring is common.

Regardless of type, an individual with sleep apnea is rarely aware of having difficulty breathing, even upon awakening. Sleep apnea is often recognized as a problem by others witnessing the individual during episodes or is suspected because of its effects on the body. Symptoms may be present for years or even decades without identification, during which time the sufferer may become conditioned to the daytime sleepiness and fatigue associated with significant levels of sleep disturbance.

Heart failure (HF) is a very common disease as reported by the ESC (European Society of Cardiology) and the HFSA (Heart Failure Society of America). The ESC represents countries with a combined population of >900 million, and there are at least 15 million patients with HF in those 51 countries. The prevalence of asymptomatic ventricular dysfunction is similar, so that HF or asymptomatic ventricular dysfunction is evident in ~4% of the population. The prevalence of HF is between 2 and 3% and rises sharply at ~75 years of age, so the prevalence in 70- to 80-year-old people is between 10 and 20%. The overall prevalence of HF is increasing also because of the ageing global population. HFSA documents that heart failure is common, but unrecognized and often misdiagnosed. It affects nearly 5 million Americans. Heart failure is the only major cardiovascular disorder on the rise. An estimated 400,000 to 700,000 new cases of heart failure are diagnosed each year and the number of deaths in the United States from this condition has more than doubled since 1979, averaging 250,000 deaths annually.

The large amount of HF incidents is naturally accompanied by a high healthcare cost. Besides cardiac diseases, respiratory diseases are widespread, where an early intervention or more straightforward diagnosis would be beneficial for both a person's health and the associated healthcare cost. The British Lung Foundation reveals the following facts:
  There are more than forty conditions which affect the lungs and/or airways and impact on a person's ability to breathe. They include, among others, lung cancer, tuberculosis, asthma, COPD (chronic obstructive pulmonary disease), cystic fibrosis, sleep apnea, avian flu, bronchiolitis;
  1 person in every 7 in the UK is affected by lung disease—this equates to approximately 8 million people;
  Respiratory disease is the second largest killer in the UK (117,456 deaths in 2004) after all non-respiratory cancers combined which only account for slightly more deaths (122,500 deaths in UK in 2004);
  Respiratory disease is the second largest killer globally after cardiovascular diseases;
  In 2020 out of 68 million deaths worldwide, 11.9 million will be caused by lung diseases;
  The UK's death rate from respiratory disease is almost double the European average and the $6^{th}$ highest in Europe;
  Deaths from occupational lung disease are rising rapidly due to a 75% increase in the number of mesothelioma deaths between 1988-1998;
  Respiratory disease is the most commonly reported long term illness in children and the third most commonly reported in adults.

Respiration monitoring is valuable in the consumer market, particularly for relaxation. Nowadays, it is more difficult to fall asleep in a relaxed manner due to irregular sleep, shift duty, performance pressure and stress. Solutions around relaxation have become more and more important. A person's state of relaxation is closely linked to his/her breathing characteristics. Since the breathing pattern changes throughout the process of falling asleep, respiration analysis can provide control parameters for sleep enhancement interventions, such as paced breathing for relaxation.

Further, since humans spend almost a third of their life sleeping, good quality sleep is essential for good health and well-being. However, lifestyle and environmental factors are increasingly causing difficulties in sleeping as discussed herein. Nowadays, there is an increased deterioration of sleep quality due to diseases, irregular sleep, shift duty, performance pressure, and stress. Poor sleep has negative effects on behavior, mood, performance, safety, mental and physical health.

Respiration analysis can be performed by a method comparable to phase-shifting interferometry, as is typically used for the quantification of depth. To do so, a light pattern is projected on the area to be analyzed. In the absence of a projected light pattern, the relationship between the observed vertical shift and the real vertical shift of reflected light coming from natural sources is analyzed. Micro movements from breathing deform this pattern of projected light from natural light significantly. If the requirements are relaxed and the image quality is sufficient, the micro movements can be extracted from the images without any additional pattern projection.

According to another embodiment of the invention, analysis of the breathing of the subjects in the common bedding largest motion areas in consecutive images, or images that are several frames apart, (the number of frames depends on the frame rate set in the camera), are identified in times of no limb movement by the subjects. When performing a motion estimation to provide motion vectors, the largest motion areas are the areas having the largest motion vectors. To identify the times of no limb movement a threshold value for the motion vectors may be applied. If the motion vectors are below the threshold value, the areas of the largest motion vectors are identified and a respiration analysis is performed only in these areas. This decreases the computational power needed for the analysis and enables implementation of the method for small monitoring devices acting as stand-alone systems.

According to another embodiment of the invention, an individual breathing analysis per subject is performed by performing an independent respiration analysis per identified largest motion area. This enables an exact monitoring of the breathing for each individual subject even when the subjects are located in close vicinity to each other, for example in a common bed or under one duvet.

According to another embodiment of the invention, the images coming from the optical sensor are segmented into boundaries of dominant chest motion. Such segmentation can be based on the results of the motion estimation and the motion vectors calculated, e.g., by assigning motion vectors having the same alignment to one segment. The alignment may vary within a definable threshold level for the assignment. It was found that in general the chest motion vectors of different subjects located in a common environment differ significantly in their alignment, so that the assignment of the vectors to different segments representing the different subjects is possible.

According to another embodiment of the invention, the optical sensor images the environment of the bed, in addition to the subjects sharing the common bed. By doing so, subject motion can be monitored right at the point when the subject is entering the monitored environment, e.g., the bedroom or the like. By constantly monitoring the motion of the subjects, assignment of the motions to the different subjects is easier since results of motion estimation coming from prior images can be taken into consideration when consecutive images, or images that are several frames apart, are analyzed.

According to another embodiment of the invention, the motion vectors resulting from the motion estimation are used to track the subjects also in the environment of the bedding. By doing so, subject motion can be monitored also when leaving the common bedding, as long as they are still in the common environment, e.g. the bedroom or the like. By constantly monitoring the motion of the subjects, assignment of the motions to the different subjects is easier since results of motion estimation coming from prior images can be taken into consideration when consecutive images, or images that are several frames apart, are analyzed.

In another aspect, the invention relates to an apparatus for monitoring movement of subjects located in a common bedding, the apparatus comprising an optical sensor, and a data processing unit, wherein the optical sensor is capable of imaging a common bedding and to deliver data of consecutive images, or images that are several frames apart, to the data processing unit, wherein the data processing unit is capable of performing a computer program comprising a set of instructions capable of causing the processing unit to perform a method as described above.

Particularly, the computer program has the capabilities of performing a motion estimation on the images received from said optical sensor by producing motion vectors indicating the local displacement of corresponding image blocks between consecutive images, or images that are several frames apart, received from said optical sensor, calculating motion clusters by measuring spatial and temporal correlations of the motion vectors, segmenting the calculated motion clusters by assignment of each motion cluster to a corresponding subject, wherein assignment of the motion clusters to the corresponding subject is based on the spatial and/or temporal similarity of the motion clusters among each other and previous segmentation results.

In another embodiment of the invention, an apparatus comprising a light projecting means, capable of projecting a light pattern on said common bedding. Preferably, the light projecting means projects light patterns at a wavelength invisible to the human eye, e.g., in the IR range of the electromagnetic spectrum.

In another aspect, the invention relates to a computer program comprising a set of instructions capable, when incorporated into a machine-readable medium, of causing an information processing system to perform the method described above. Particularly, the computer program has the capabilities to perform a motion estimation on the images received from an optical sensor by producing motion vectors indicating the local displacement of corresponding image blocks between consecutive images, or images that are several frames apart, received from said optical sensor, calculating motion clusters by measuring spatial and temporal correlations of the motion vectors, segmenting the calculated motion clusters by assignment of each motion cluster to a corresponding subject, wherein assignment of the motion clusters to the corresponding subject is based on the spatial and/or temporal similarity of the motion clusters among each other and previous segmentation results.

Monitoring breathing can be useful for many sleep/relaxation applications, such as a closed-loop paced breathing device or other relaxation devices, a device for monitoring apnea or snoring, a sleep coach, a sleep depth monitor, a contactless "sleep quality scorer" etc. Monitoring movement can also be useful for many sleep/relaxation applications, such as systems that respond to the sleep/wake state of a person (e.g. a system that turns off when a person falls asleep), a device for monitoring periodic limb movements, a sleep depth monitor, a contactless "sleep quality scorer", etc. These are typically devices targeted at monitoring or influencing one user; however, many people share their bed with others. This invention is further relevant for systems that are targeted at two people, e.g., a paced breathing device or other relaxation device that is designed for use by two (or more) people.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
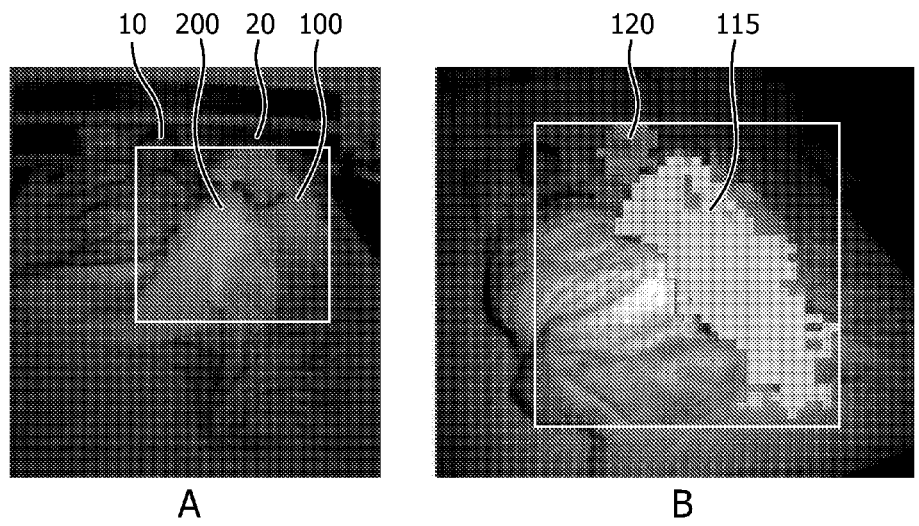
FIG. 1 shows motion vectors of two sleeping subjects.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

FIG. 1 shows motion vectors of two sleeping subjects 10 and 20. Motion vectors of two sleeping subjects, recorded in a real home situation, are color/number coded. Different colors/numbers indicate different motion vectors. The two subjects are lying close to each other and are making movements while sleeping. FIG. 1A: The different type of motion vectors can be used to segment the subjects from each other, i.e., the blue area 100 belongs to the right subject, the purple area 200 to the left subject. FIG. 1B: Mainly, the right subject is moving which is visible due to the strong motion vectors 100 on his/her side. The head moves (red area 115) in a different direction from the body (green area 120).

Figure 2:
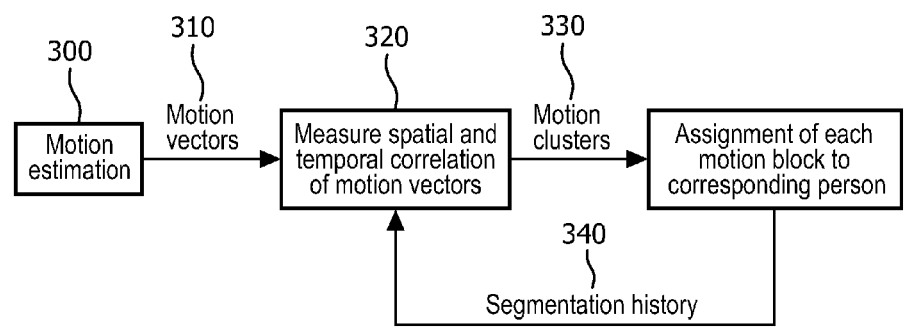
FIG. 2 shows a block diagram of assigning movements to the correct subjects.

FIG. 2 shows a block diagram of assigning movements to the correct subject. After a motion estimation 300 is performed on the image data received from an optical sensor resulting in motion vectors 310, e.g., by an optical flow algorithm, the spatial and temporal correlations between the motion vectors 310 are measured in step 320. Motion vectors 310 having the same alignment, within a tolerance extent, are merged to motion clusters 330. These motion clusters 330 are assigned to the corresponding subject. For increasing the accuracy of the assignment as well as for reducing the needed computational power, the segmentation history 340 of a previous image analysis is taken into consideration when measuring the spatial and temporal correlations of the motion vectors 310.

Figure 3:
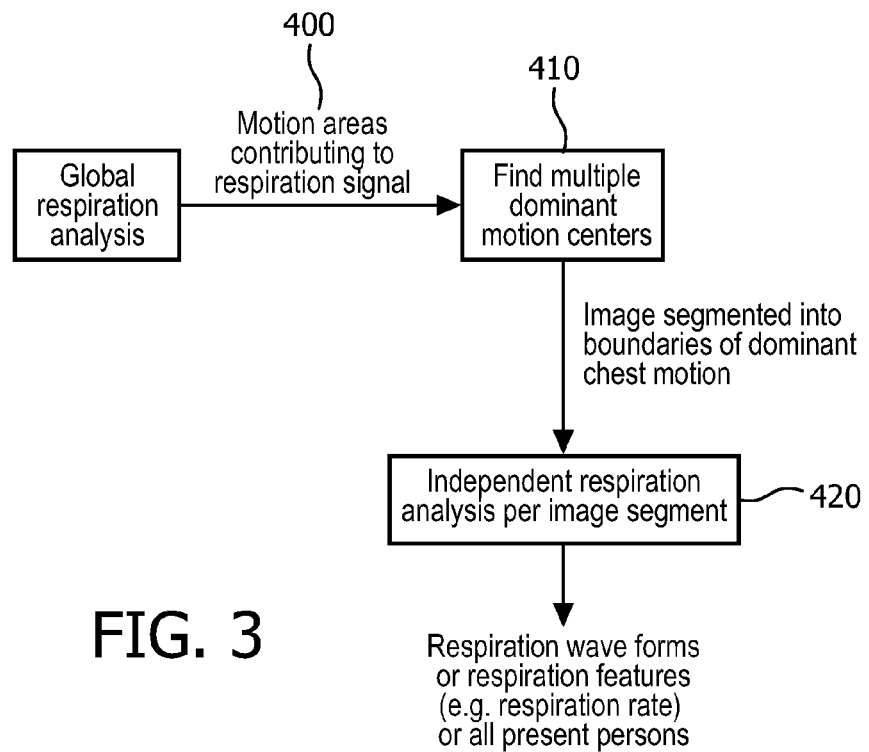
FIG. 3 shows a block diagram of extracting individual respiration signals.
Figure 8:
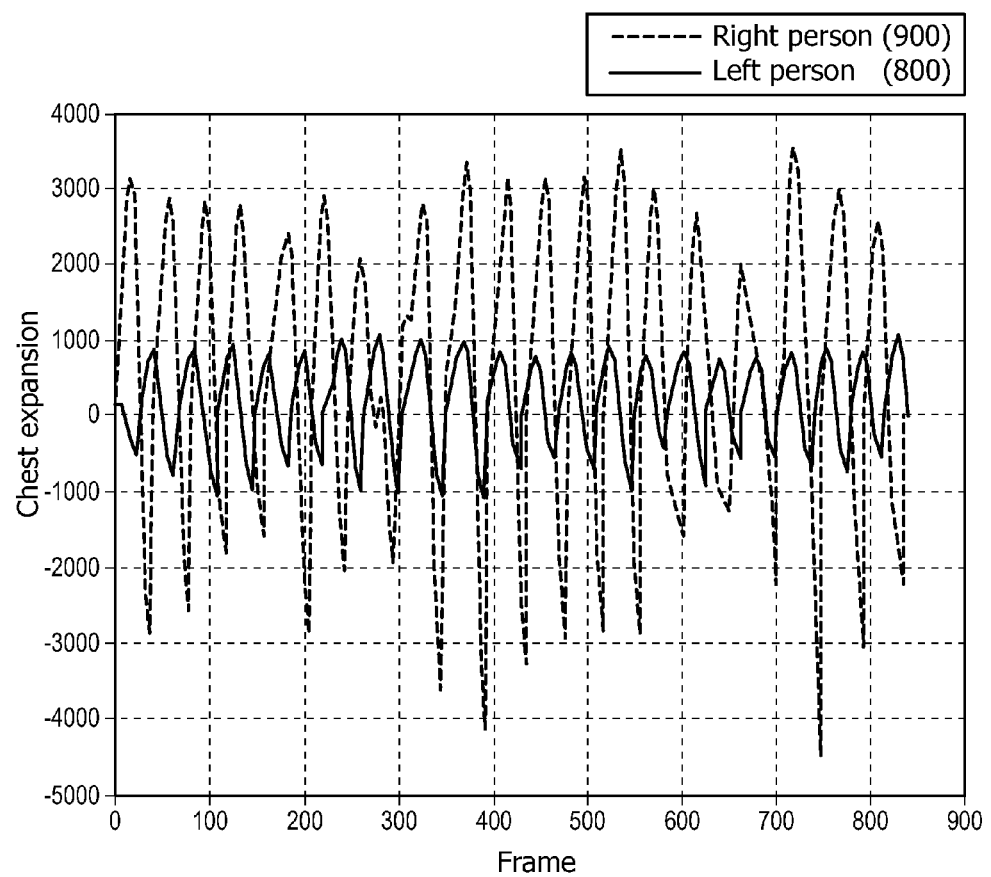
FIG. 8 shows a diagram representing individually processed respiration signals.

FIG. 3 shows a block diagram of extracting individual respiration signals. In order to extract the breathing wave form per subject with one sensor, the approach described in FIG. 3 is suggested. Any type of optical-sensor based respiration algorithm can be applied, e.g., by a method comparable to phase-shifting interferometry, as it is typically used for the quantification of depth. To do so, a light pattern is projected on the area to be analyzed. In the absence of a projected light pattern, the temporal inter-relationship between the same image areas (e.g., image blocks) is observed, e.g. the amount of reflected infrared light will vary over time in a breathing area. Micro movements from breathing deform the pattern of projected light from natural light significantly. The motion areas 400 contributing mostly to the global respiration signal of the entire image (see FIG. 4 for the original input image) can be analyzed and the dominant motion centers 410 are obtained (see highlighted areas in FIG. 5, 6, 7). The image is further segmented into the found motion centers and the respiration analysis algorithm 420 is performed on the multiple (two or more, depending on the number of subjects in bed) image regions independently. This results in two independent wave forms as shown in FIG. 8. The wave forms have been visually verified by subjectively assessing the breathing movement in the images.

Figure 4:
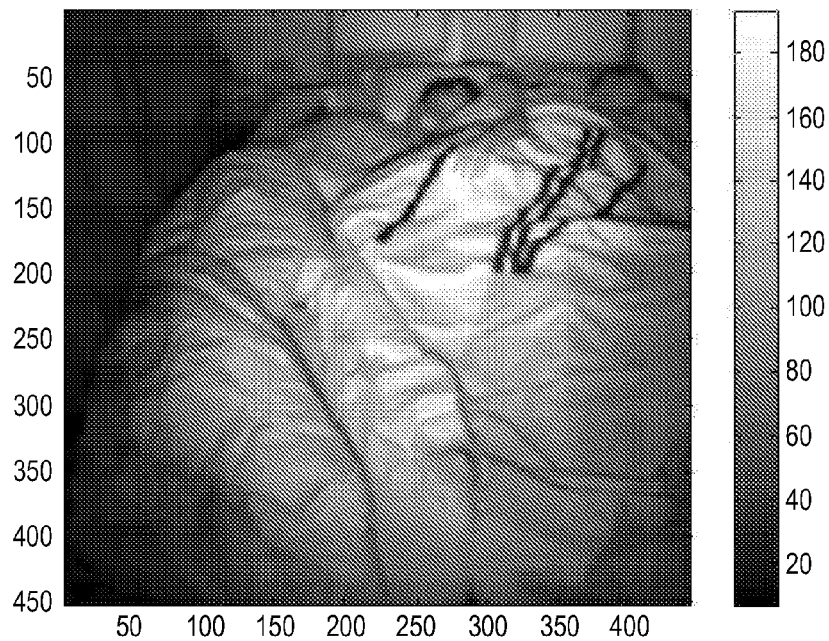
FIG. 4 shows a grey-scale image from an over-night sleep sequence.

FIG. 4 shows a grey-scale image from an over-night sleep sequence. This original grey-scale image from the over-night sleep sequence with two subjects lying closely side-by-side is an example for the consecutive images, or images that are several frames apart, used as input for the motion estimation as described above.

Figure 5:
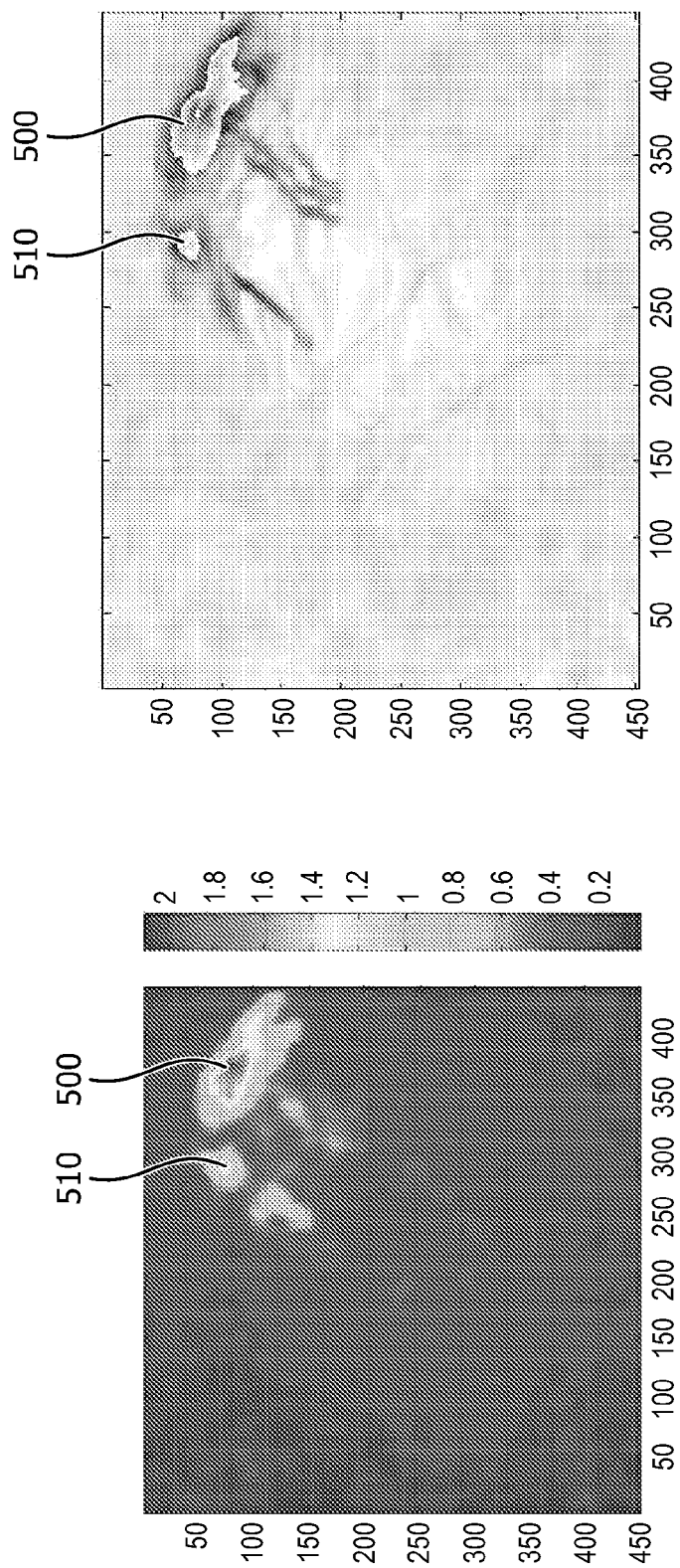
FIG. 5 shows an instance during a respiration cycle.

FIG. 5 shows an instance during a respiration cycle. It is an instance during the respiration cycle when the chests of both subjects are moving. In the left picture the highlighted motion areas 500, 510 during respiration monitoring are shown, while the right picture shows an overlay of high chest motion output 500, 510 with the original grey-scale image (right).

Figure 6:
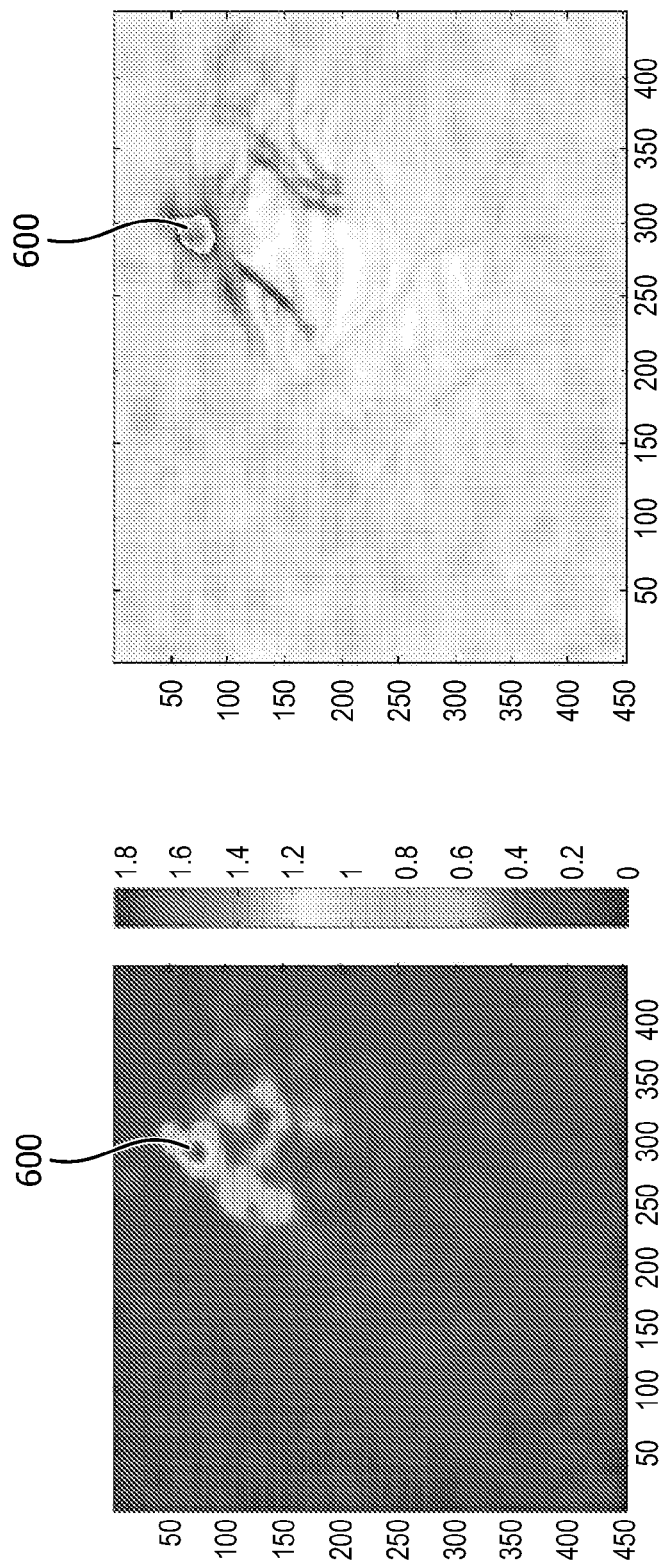
FIG. 6 shows another instance during a respiration cycle.

FIG. 6 shows another instance during a respiration cycle. Here, the instance during the respiration cycle is shown when the chest of the left subject is moving. Highlighted motion areas during respiration monitoring 600 (left) and an overlay of the high chest motion output 600 with the original grey-scale image (right) are shown.

Figure 7:
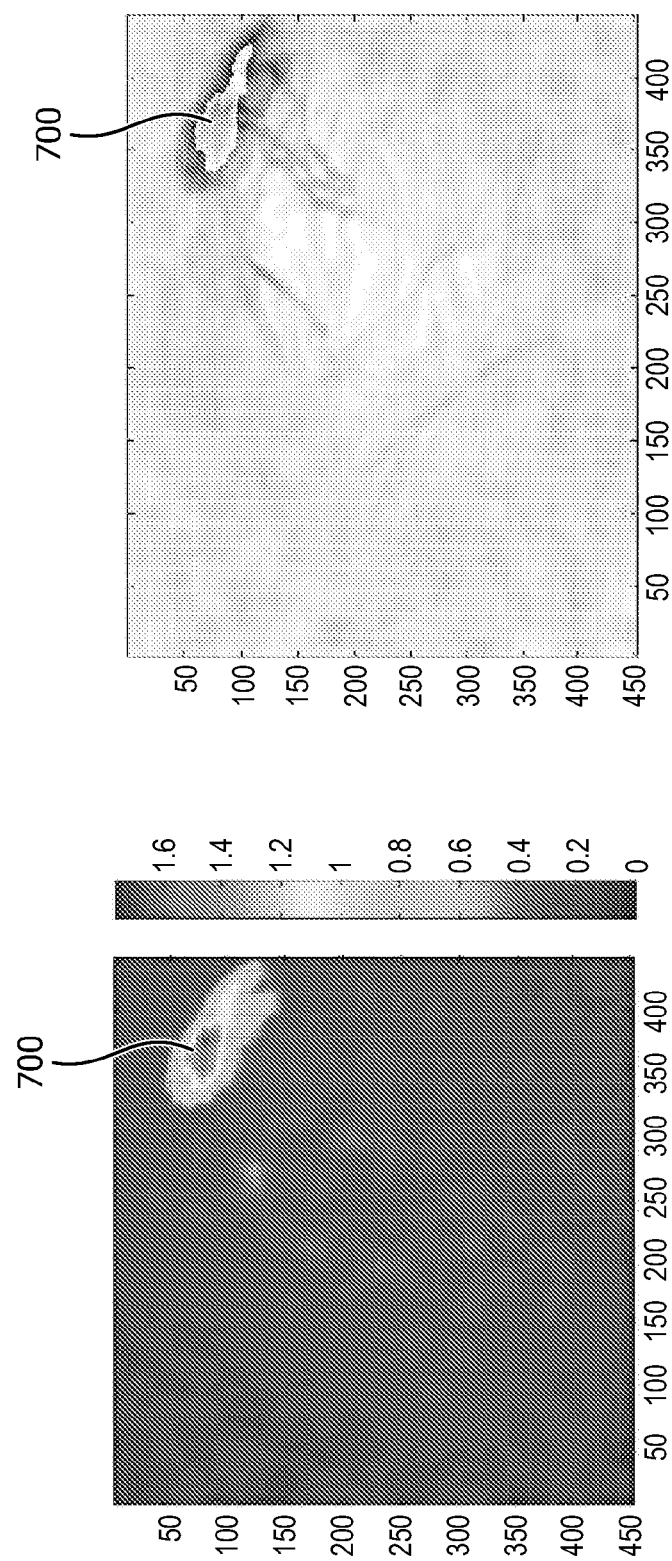
FIG. 7 shows another instance during a respiration cycle.

FIG. 7 shows another instance during a respiration cycle. Here, the instance during the respiration cycle is shown when the chest of the right subject is moving. Highlighted motion areas during respiration monitoring 700 (left) and the overlay of high chest motion output 700 with original grey-scale image (right) are shown.

FIG. 8 shows a diagram representing the individually processed respiration signals. Individually processed respiration signals of the two sleeping subjects after segmenting the image areas and assigning them to the corresponding subject are depicted. It is visible that the left subject (black, 800) has a higher respiration rate than the right subject (blue, 900) and is sometimes breathing in the same phase as the right subject and sometimes in counter phase. Note that the scale in amplitude can be neglected since the respiratory signal is not normalized.

The invention claimed is:

1. A method for monitoring movement of subjects located in a common bedding, said subjects being persons, animals, or a combination of persons and animals, the method comprising the steps of:
    imaging the bedding by an optical sensor;
    performing a motion estimation by producing motion vectors indicating the local displacement of corresponding image blocks between consecutive images, or images that are several frames apart, received from said optical sensor;
    calculating motion clusters by measuring spatial and temporal correlations of the motion vectors;
    segmenting the calculated motion clusters by assigning each motion cluster to a corresponding subject,
    wherein an assignment of the motion clusters to the corresponding subject is based on any one or a combination of the spatial similarity and temporal similarity of the motion clusters among each other, and
    wherein a respiration analysis is performed for each subject in the common bedding based on data of the consecutive images, or several images apart, provided by the optical sensor in that the analysis of the breathing of two or more of the subjects in the common bedding, is performed by using the largest motion areas in said consecutive images, or images that are several frames apart, which are identified during times of no limb movement by the subjects.

2. The method according to claim 1, wherein the segmentation results of prior images are taken into consideration for the assignment of motion clusters to a corresponding subject in a subsequent image.

3. The method according to claim 1, wherein said images are segmented into boundaries of dominant chest motion.

4. The method according to claim 1, wherein an individual breathing analysis per subject is performed by executing an independent respiration analysis per identified said largest motion area.

5. The method according to claim 4, wherein a light pattern is projected on said common bedding and said pattern of projected light is deformed such that the micro movements due to breathing by one subject or the other subject can be extracted from the images.

6. The method according to claim 1, wherein the optical sensor additionally images also the environment of the bedding in addition to said two or more subjects sleeping in said common bedding.

7. The method according to claim 6, wherein the motion vectors resulting from the motion estimations are used to track the subjects within said bedding environment.

8. The method according to claim 1, wherein said motion estimation is performed by at least one algorithm from the group consisting of block-matching algorithm, optical flow estimation, maximum a posteriori probability estimation, Markov random field estimation, mean square error calculation, sum of absolute difference calculation, mean absolute differences calculation, sum of squared error calculation, or sum of absolute transformed differences calculation.

9. An apparatus for monitoring movement of subjects located in a common bedding environment, the apparatus comprising a data processing unit, the data processing unit configured to receive data of consecutive images, or images that are several frames apart, from an optical sensor and corresponding to the common bedding, wherein the data processing unit is configured to:
perform a motion estimation by producing motion vectors indicating the local displacement of corresponding image blocks between consecutive images, or images that are several frames apart, received from said optical sensor;
calculate motion clusters by measuring spatial and temporal correlations of the motion vectors;
segment the calculated motion clusters by assigning each motion cluster to a corresponding subject,
wherein an assignment of the motion clusters to the corresponding subject is based on any one or a combination of the spatial similarity and temporal similarity of the motion clusters among each other.

10. The apparatus according to claim 9, wherein the data processing unit is further configured to perform a respiration analysis for each subject in the common bedding based on data of the consecutive images, or several images apart, provided by the optical sensor in that the analysis of the breathing of two or more of the subjects in the common bedding, is performed by using the largest motion areas in said consecutive images, or images that are several frames apart, which are identified during times of no limb movement by the subjects.

11. The apparatus according to claim 10, wherein a threshold value for motion vectors corresponding to limb movement is defined, and based on the data processing unit determining that the motion vectors corresponding to limb movement is less than the threshold value, the data processing unit is configured to identify areas of the subjects where motion vectors are largest and perform the respiration analysis only for those identified areas.

12. The apparatus according to claim 11, wherein the data processing unit is further configured to perform the respiration analysis independently for each of the subjects per identified largest motion area.

13. The apparatus according to claim 9, wherein the data processing unit is further configured to analyze a relationship between an observed vertical shift and a real vertical shift of reflected light from a natural source.

14. The apparatus according to claim 9, wherein the data processing unit is further configured to analyze a deformation of reflected light corresponding to a projected light pattern based on micro movements from breathing by the subjects.

15. The apparatus according to claim 9, wherein the data processing unit is further configured to segment the images from the optical sensor into boundaries of dominant chest motion by assigning motion vectors having a same alignment to one segment.

16. The apparatus according to claim 15, wherein the alignment of the motion vectors for one of the subjects is different than the alignment for another of the subjects.

17. The apparatus according to claim 9, wherein the data processing unit is further configured to associate motion vectors having a same alignment to one of the motion clusters.

18. The apparatus according to claim 9, wherein the data processing unit is configured to receive data corresponding to low resolution images.

19. A computer program comprising a set of instructions capable, when incorporated in a non-transitory machine-readable medium, of causing a a data processing unit to:
receive data of consecutive images, or images that are several frames apart, from an optical sensor, the images corresponding to plural subjects in a common bedding;
perform a motion estimation by producing motion vectors indicating the local displacement of corresponding image blocks between consecutive images, or images that are several frames apart, received from said optical sensor;
calculate motion clusters by measuring spatial and temporal correlations of the motion vectors;
segment the calculated motion clusters by assigning each motion cluster to a corresponding subject,
wherein an assignment of the motion clusters to the corresponding subject is based on any one or a combination of the spatial similarity and temporal similarity of the motion clusters among each other.

* * * * *